(12) United States Patent
Pariseau

(10) Patent No.: US 9,158,652 B2
(45) Date of Patent: Oct. 13, 2015

(54) INTELLIGENT MODULES IN A PARTICLE COUNTER

(71) Applicant: Particles Plus, Inc., Canton, MA (US)

(72) Inventor: David Pariseau, Los Altos, CA (US)

(73) Assignee: Particles Plus, Inc., Stoughton, MA (US)

( * ) Notice: Subject to any disclaimer, the term of this patent is extended or adjusted under 35 U.S.C. 154(b) by 0 days.

(21) Appl. No.: 14/214,889

(22) Filed: Mar. 15, 2014

(65) Prior Publication Data

US 2014/0281659 A1 Sep. 18, 2014

Related U.S. Application Data

(60) Provisional application No. 61/786,651, filed on Mar. 15, 2013.

(51) Int. Cl.
*G01N 15/02* (2006.01)
*G06F 11/34* (2006.01)

(52) U.S. Cl.
CPC .................................. *G06F 11/3452* (2013.01)

(58) Field of Classification Search
CPC .......... G01N 15/0205; G01N 15/0211; G01N 15/1459; G01N 2021/4716; G01N 15/1434
USPC ......................................................... 356/336
See application file for complete search history.

(56) References Cited

U.S. PATENT DOCUMENTS

| | | | | |
|---|---|---|---|---|
| 2003/0009334 | A1* | 1/2003 | Printz et al. | 704/256 |
| 2004/0068389 | A1* | 4/2004 | Kleefstra | 702/155 |
| 2006/0071803 | A1* | 4/2006 | Hamburger et al. | 340/630 |

* cited by examiner

*Primary Examiner* — Tarifur Chowdhury
*Assistant Examiner* — Md Rahman

(57) ABSTRACT

An airborne, gas, or liquid particle sensor with one or more intelligent modules either within the instrument or attached to the instrument. These modules comprising sub-systems with local controllers or memory.

17 Claims, 2 Drawing Sheets

INTELLIGENT MODULES IN A PARTICLE COUNTER

CROSS-REFERENCE TO RELATED APPLICATION

This application claims priority to U.S. Provisional Application Ser. No. 61/786,651 filed on Mar. 15, 2013, titled INTELLIGENT MODULES IN A PARTICLE COUNTER by inventor David Pariseau, the entire disclosure of which is hereby incorporated herein by reference.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,876, filed herewith on Mar. 15, 2014, titled MULTIPLE PARTICLE SENSORS IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban.

BACKGROUND

Particle counters have been used for decades in manufacturing or industrial applications to measure particulate quantities in air, gases or liquids. Typically such counters would also bin particulates by size. These size bins vary by application and often by instrument. A particle counter has at least one size channel and popular counters can have 6 or more channels. Typically these size channels discriminate pulses based on the pulse height of the incoming signal. The pulse height refers to the peak voltage of the signal. Sometimes there is also rudimentary discrimination of pulse width, often in hardware. These systems provide a go/no-go qualification for an incoming pulse, typically they are implemented in hardware and provide a simple gate function such that pulses below a minimum duration are excluded from counting. The intent is to reject noise, typically at the most sensitive resolution where the signal-to-noise ratio is the poorest. Therefore what is needed is a system and method that allows rejection of noise at the most sensitive resolutions for particle.

SUMMARY

In accordance with the various aspects of the present invention, a system and method are provided for rejection of noise at the most sensitive resolutions, including for particle detection. The foregoing is a summary and, hence. includes, by necessity, simplifications, generalizations and omissions of detail. Those skilled in the art will appreciate that the summary is illustrative only and is not intended to be in any way limiting.

BRIEF DESCRIPTION OF THE DRAWINGS

The foregoing summary as well as the following detailed description is better understood when read in conjunction with the appended drawings. For the purpose of illustrating the invention, there is shown in the drawings exemplary constructions of the invention; however, the invention is not limited to the specific various aspects, embodiments, methods and instrumentalities disclosed in the drawings.

DETAILED DESCRIPTION

Figure 1:
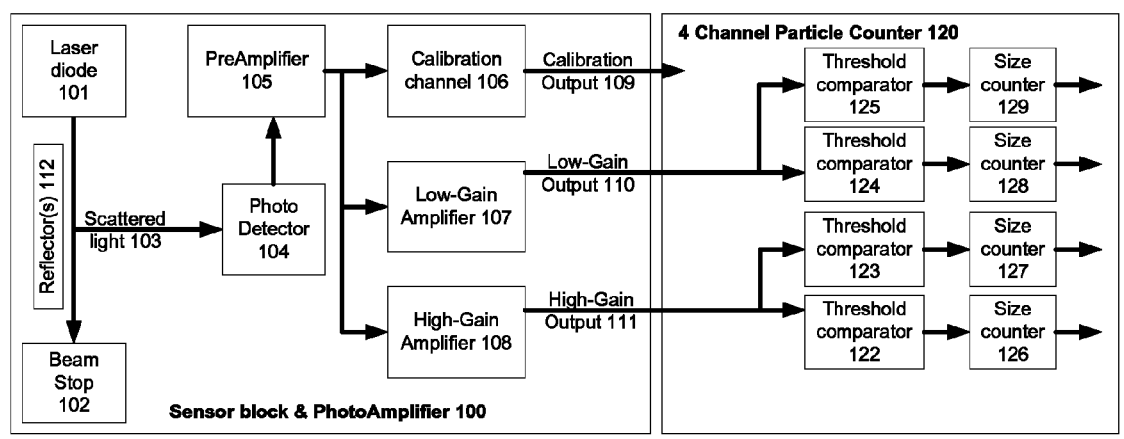
FIG. 1 shows a system in accordance with the various aspects of the present invention.

It is noted that, as used in this description, the singular forms "a," "an" and "the" include plural referents unless the context clearly dictates otherwise. Reference throughout this specification to "one aspect," "another aspect," "at least one aspect," "various aspects," "further aspect," "one embodiment," "an embodiment," "certain embodiments," or similar language means that a particular aspect, feature, structure, or characteristic described in connection with the embodiment or embodiments is included in at least one aspect or embodiment of the present invention. Thus, appearances of the phrases "in accordance with one aspect," "in accordance with various aspects," "in accordance another aspect," "one embodiment," "in at least one embodiment," "in an embodiment," "in certain embodiments," and similar language throughout this specification may, but do not necessarily, all refer to the same embodiment.

In accordance with the various aspects of the present invention, a device includes a computing device. As referred to herein, the devices may be part of a system or the system. It may be implemented to include a central processing unit (e.g., a processor), memory, input devices (e.g., keyboard and pointing devices), output devices (e.g., display devices), and storage device (e.g., disk drives). The memory and storage device are computer-readable media that may contain instructions or code that, when executed by the processor or the central processing unit, cause the device to perform certain tasks. In addition, data structures and message structures may be stored or transmitted via a data transmission medium, such as a signal on a communications link. Various communications channels may be used (e.g., the Internet, a local area network (LAN), a wide area network (WAN), or a point-to-point dial-up connection, or any other wireless channel or protocol) to create a link.

In accordance with the various aspects of the present invention, the device or system may be use various computing systems or devices including personal computers, server computers, hand-held or laptop devices, multiprocessor systems, microprocessor based systems, programmable consumer electronics, network personal computers (PCs), minicomputers, mainframe computers, distributed computing environments that include any of the above systems or devices, and the like. In accordance with the various aspects of the present invention, the device or system may also provide its services to various computing systems such as personal computers, cell phones, personal digital assistants, consumer electronics, home automation devices, and so on.

In accordance with the various aspects of the present invention, the device or system may be described in the general context of computer-executable instructions, such as program modules or code, which is executed by one or more computers or devices. Generally, program modules include routines, programs, objects, components, data structures, and so on that perform particular tasks or implement particular data types. Typically, the functionality of the program modules may be combined or distributed as desired in various embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present invention. The upper and lower limits of these smaller ranges may independently be included in the smaller ranges and are also encompassed within the aspects of the present invention, subject to any specifically excluded limit in the stated range. Where the stated range includes one or both of the limits, ranges excluding either or both of those included limits are also included in the aspects of the present invention.

Referring now to FIG. 1 and in accordance with the various aspects of the present invention, an example of a four-channel particle counter front-end 150 is shown. In this example a beam present between the laser diode (101) and the beam stop (102) scatters light (103) as particles cross that beam. Typically the scattered light (103) is focused by one or more reflectors (112) onto the face of a photo-diode (104) on a photo-amplifier board (100). The tiny current in the photo-diode is then pre-amplified, usually by a trans-impedance amplifier (105). The pre-amplified signal is usually available on a calibration channel (106) for use during calibration. The pre-amplifier (105) signal is also sent to one or more amplifiers. In this case there are two, a low-gain channel (107) and a high-gain channel (108). These amplifiers further increase the signal amplitude and transmit send it, often, to a separate particle counting board (120). On this board the incoming pulse signals are sorted into size bins.

In accordance with the various aspects and embodiments of the present invention, in this example there are four channels, two channels (122,123) connected to the high-gain amplifier (111) and two channels (124,125) connected to the low-gain amplifier (110). The threshold comparators (122,123,124, 125) are setup during the calibration phase so that they each channel counts pulses above some threshold. This can be a manual process with manual adjustment of a potentiometer, or a programmatic process where firmware would set a digital potentiometer or digital-to-analog converter. The counter outputs (126,127,128,129) would then be read by microcontroller and displayed to the user, or transmitted to an external system.

A similar system functions for gases other than air, and liquids. It also functions for counters that use a light-blocking rather than a light-scattering architecture, except that pulses in light-blocking systems see a decrease in light as the particles pass through the beam.

These are designed with dedicated hardware performing the various functions within a particle counter system, also referred to as "particle counter." In the event where various modules are combined in such counters new products are typically created with each of these having unique firmware.

Modules are sub-systems within an instrument that are self-contained physical devices that can be connected to (e.g., physically coupled) and disconnected (e.g., physically decoupled) from an instrument board. They would typically have local power management, local processing, perhaps local sensing and/or memory.

In certain embodiments, instruments are configured during final assembly by interconnecting off-the-shelf modules and/or replacing or adding a module.

In certain embodiments, particle counter architecture is implemented with intelligent modules. These modules, as previously noted, are distinct physical units connected to the main counter board(s) either within the instrument or attached to the instrument. These modules have some local processing and are configured to communicate to the instrument, not only processed data, but at least one of configuration, status, and statistical information.

This allows an instrument to configure itself for operation based upon which modules are currently installed or attached to it. So, this type of architecture of the particle counter allows the following:

possible channel sizes in configuration screens would be a function of which intelligent particle sensor block was installed within an instrument, and changing blocks would change the options available, possible analysis and reporting functions enabled or disabled based on the parametrics recorded in the front-end sensor block (pulse height, pulse-width, time-of arrival, counts/channel/second), which is communicated by the sensor block module, battery life estimate is a function of which intelligent battery was installed in an instrument and factors such as battery age, previous charge/discharge profiles, etc. is used to provide for more accurate measurements. And, since such information resides on the module itself, the information would travel with the battery if it was moved from one instrument to another, in the case of external interfaces, the instrument could display which of these are installed and what the interface options are for each. For example, this includes 4-20 ma outputs, analog voltage outputs, RS-232, RS-422, RS-485, modbus, ethernet, USB, alarm outputs, interlock inputs, optical links, wireless, etc. The module communicates its functionality and the instrument allows it to be configured and integrated into the instrument.

By making the configuration a generic set of services, integrating a broad range of modules is implemented in such a way as to not require any custom code to be generated within the instrument for a new module. This is accomplished by formalizing the modular interface. For example, a module identifies itself and then lists possible services it has to offer and request the resources it requires to implement these. In another example, a module provides the GUI text fields required for configuration of its internal parameters or the display of its internal settings. In this manner the instrument code is written to handle generic device types (much as device-drivers are currently written for classes of devices in computer systems). Such classes of devices include: sensor blocks, batteries, external sensors, external interfaces, touch-screen or gesture modules, printers, external memory devices, etc.

Figure 2:
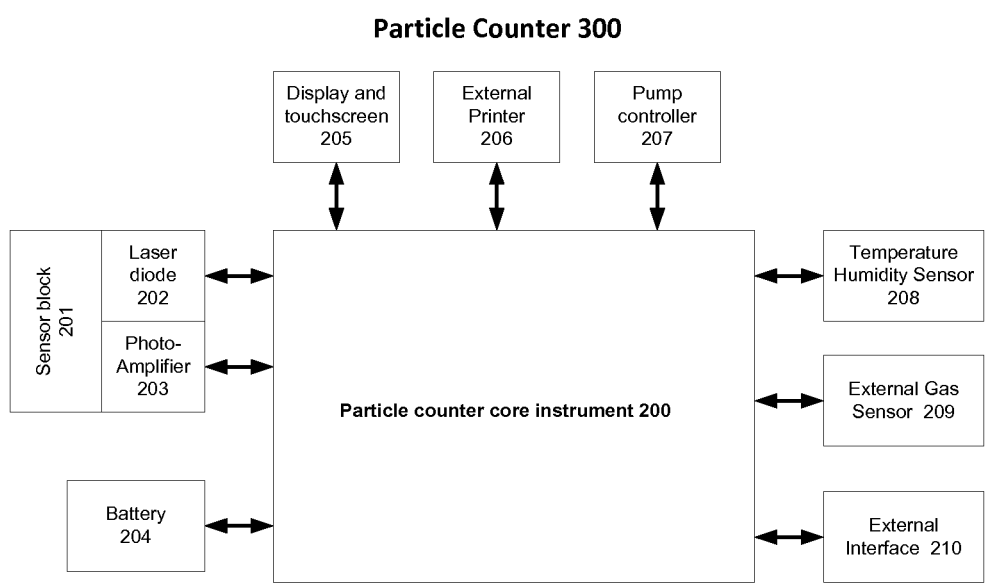
FIG. 2 shows a photo amplifier in accordance with the various aspects of the present invention.

There are a large number of intelligent modules possible, and this list is not exhaustive. In certain embodiments, modules are configurable and extensible firmware base within an instrument in order to create an instrument that provides significant flexibility. This flexibility could:

simplify service by simplifying replacement of failed modules, since modules are intelligent it reduces the need for local calibration or factory installation, extend an instrument's life by allowing a user to replacing existing modules that cannot meet changing requirements with more capable or powerful modules that can, provide a lower-cost of entry, since a basic instrument could be purchased and later upgraded to provide more advanced functionality without having to buy this functionality at the time of purchase, Referring now to FIG. 2, in certain aspects and embodiments, a particle counting (300) includes a core instrument board (200) with a number of installed modules. In the example much of the functionality is shown in modular format, though some of these modules are present within the core instrument board (200) instead of as modules. It is also possible to have a module's functionality present within the core instrument board (200) and still be present as a module, since in some cases it may be meant to supersede the local functionality by replacing that with updated functionality, or specialized functionality, or even to circumvent local errors or failures.

In the above non-limiting example, a single core instrument board (200) provides local resources, one or more controllers, and power management and/or distribution. Into this instrument board are connected various modules (202,203, 204,205,206,207,208,209,210).

Here, the sensor block (201) has two modules connected to it. One controls the laser diode (202). This module provides details on the laser diode for configuration and reporting purposes, such as a laser diode manufacturer, the date of final assembly, the date of last calibration or service for the diode, how many hours the laser diode has been on since last serviced, the laser diode's lifetime hours, the current power setting, the min-max power setting for this diode, the total energy driven by this diode in its lifetime, etc. This module might also have a list of faults or errors encountered since last reset. In this architecture this information resides on the module itself, so if it is moved from one instrument to another all the settings, history, statistics travels with the module itself, which makes troubleshooting or analyzing performance or module lifetime much simpler and much more accurate.

The PhotoAmplifier module (203), provides model number, minimum and maximum particle size, lifetime hours, details on the accuracy of the measurement, etc. Depending on the resources present in this module, it allows the instrument to setup Threshold comparators, clear or read counters, read a calibration signal, etc.

A battery module (204), allows different batteries to be used in the same instrument. Batteries with different capacities, chemistries, even maximum voltages might all be candidates for providing local power. The batteries would have at least local storage, or they have local processing. Local storage holds configuration information that the instrument uses to determine the battery operating parameters in order to implement battery management for this battery. A portion of the local storage is used by the instrument to record statistical information on minimum, maximum cycles, last 'n' cycles, any faults or errors, etc., for example. Based on this information, the instrument can provide more accurate battery information to the user. The battery module (204) might also have local processing which would manage much of the above and provide a higher-level interface to the instrument, perhaps simply reporting a calculated state-of-charge (SOC) percentage value on demand and managing the charging and power management internally.

A separate display and touchscreen module (205) allows various displays and touchscreens to be used with a core instrument board. This creates products with diverse requirements. Typically smaller handheld instruments use a smaller display and touchscreen, while larger portable or fixed instruments use significantly larger displays and touchscreens. In some cases the touchscreen technology must suit a particular application. For example, in the case of larger portable models, typically a protective overlay is placed over the display glass (to allow cleaning with solvents in a cleanroom), and this precludes using less-expensive resistive touchscreens. Having a configurable Display or Touchscreen module (205) allows for using an appropriate module for an application without requiring a redesign of the instrument board.

A printer module (206) allows for various external printers to be used with an instrument. It also allows for replacing obsolete printers with newer models while still allowing support for the older models.

A pump controller module (207) allows for different pumps to be used for an instrument. This allows for smaller and less expensive pumps to be installed and used in low-cost/low-flow applications and larger higher-cost/higher-flow pumps to be used in more demanding applications without requiring changes to the main instrument board.

When various external temperature and humidity sensors (208) are used with these instruments; they can vary significantly in cost based on accuracy and resolution. This allows an instrument to offer options for these and recognize which of these is attached to the instrument and process the incoming data accordingly.

Other auxiliary sensors are also possible, like gas sensors (209) or air flow sensors, pressure sensors, and by having intelligence or local storage on these to identify them, the instrument can process the data and format/report it correctly. Local processing and a generic interface allow (as previously described) new sensors to be added to an instrument without requiring any changes to the core instrument firmware.

External interfaces as previously noted comprises a host of possibilities, as noted these might include: 4-20 ma outputs, analog voltage outputs, RS-232, RS-422, RS-485, modbus, ethernet, USB, alarm outputs, interlock inputs, optical links, wireless, etc. The module would communicate its functionality and the instrument would allow it to be configured and integrated into the instrument.

While various embodiments have been described above, it should be understood that they have been presented by way of example only, not limitation, and various changes in form and details may be made. Any portion of the device, instrument, apparatus and/or methods described herein may be combined in any combination, except mutually exclusive combinations. The aspects and embodiments described herein can include various combinations and/or sub-combinations of the functions, components and/or features of the different embodiments described. For example, multiple, distributed processing systems can be configured to operate in parallel.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

It will be apparent that various aspects of the present invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the aspects disclosed in the teachings of the present invention and certain embodiments, a program or code may be noted as running on a device, an instrument, a system, or a computing device, all of which are an article of manufacture. Additional examples of an article of manufacture include: a server, a mainframe computer, a mobile telephone, a multimedia-enabled smartphone, a tablet computer, a personal digital assistant, a personal computer, a laptop, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform tasks and methods. Furthermore, an article of manufacture (e.g., device) includes a non-transitory computer readable medium having a series of instructions, such as computer readable program steps or code, which is encoded therein. In certain aspects and embodiments, the non-transitory computer readable medium includes one or more data repositories, memory, and storage, including non-volatile memory. The non-transitory computer readable medium includes corresponding computer readable program or code and may include one or more data repositories. Processors access the computer readable program code encoded on the corresponding non-transitory computer readable mediums and execute one or more corresponding instructions. Other hardware and software components and structures are also contemplated.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A configurable particle counting instrument comprising:
   at least one airstream chamber;
   at least one light source focused into a beam that passes through the airstream chamber;
   at least one photo-detector within the airstream chamber, the photo-detector detects changes in light as airborne particulates pass through the beam;
   at least one amplifier in communication with the photo-detector, the amplifier converts signals from the photo-detector into amplified electrical pulses;
   at least one particulate size channel, where the volume of air and light intensity are used in conjunction with the amplified electrical pulses to infer particulate counts for the particulate size channel;
   a core instrument board in communication with the particulate size channel, the core instrument board including at least one communications interface; and
   at least one module coupled through the communications interface with the core instrument board, the module including an onboard microcontroller and memory, where the module provides at least configuration information to configure operating parameters.

2. The configurable particle counter of claim 1, wherein the module providing the configuration information is a particle sensing module.

3. The configurable particle counter of claim 1, wherein the module providing the configuration information is a laser diode module.

4. The configurable particle counter of claim 1, wherein the module providing the configuration information is a pump controller module.

5. The configurable particle counter of claim 1, wherein the module providing the configuration information is a battery module.

6. The configurable particle counter of claim 1, wherein the module providing the configuration information is a display module.

7. The configurable particle counter of claim 1, wherein the module providing the configuration information is a printer module.

8. The configurable particle counter of claim 1, wherein the module providing the configuration information is a temperature module.

9. The configurable particle counter of claim 1, wherein the module providing the configuration information is a temperature and humidity module.

10. The configurable particle counter of claim 1, wherein the module providing the configuration information is a gas sensing module.

11. The configurable particle counter of claim 1, wherein the module providing the configuration information is an external interface module.

12. The configurable particle counter of claim 11, wherein the external interface module provides serial interfaces that includes at least one of RS-232, RS4-22, and RS-485.

13. The configurable particle counter of claim 11, wherein the external interface module provides an analog input.

14. The configurable particle counter of claim 11, wherein the external interface module provides an analog output that includes at least 4-20 ma.

15. The configurable particle counter of claim 11, wherein the external interface module provides an analog output that includes voltage.

16. The configurable particle counter of claim 11, wherein the external interface module provides wired intelligent serial interfaces including at least one of Ethernet and USB.

17. The configurable particle counter of claim 11, wherein the external interface module provides wireless intelligent serial interfaces that includes at least one of Ethernet, Bluetooth and Zigbee.

* * * * *